(12) United States Patent
Yoon et al.

(10) Patent No.: US 6,342,638 B1
(45) Date of Patent: Jan. 29, 2002

(54) TRIARYLPHOSPHINE OXIDE DERIVATIVES CONTAINING FLUORINE SUBSTITUENTS

(75) Inventors: Tae-Ho Yoon; Kwang Un Jeong, both of Kwangju Kwangyeok-si (KR)

(73) Assignee: Kwangju Institute of Science and Technology, Kwangju Kwangyeok-Si (KR)

( * ) Notice: Subject to any disclaimer, the term of this patent is extended or adjusted under 35 U.S.C. 154(b) by 0 days.

(21) Appl. No.: 09/695,070

(22) Filed: Oct. 25, 2000

(30) Foreign Application Priority Data

Nov. 16, 1999 (KR) ......................................... 1999-50831

(51) Int. Cl.[7] .................................................. C07F 9/53
(52) U.S. Cl. .......................... 568/14; 568/15; 528/287
(58) Field of Search ..................... 568/14, 15; 528/286, 528/287

(56) References Cited

PUBLICATIONS

CA:133:282360 abs of Polym Material Sci Eng by Yoon et al 83 pp. 377–378 Mar. 26, 2000.*
CA:120:245502 abs of JP05239076 Sep. 1993.*

* cited by examiner

Primary Examiner—Jean F. Vollano
(74) Attorney, Agent, or Firm—Rosenberg, Klein & Lee

(57) ABSTRACT

The invention relates to triarylphosphine oxide derivatives containing fluorine substituents that are useful as a monomer in preparation of polymers with improved properties such as chemical resistance and electrical insulating property as well as adhesiveness and flame retardancy. The triarylphosphine oxide derivatives containing fluorine substituents are represented by the chemical formula 1:

[Chemical Formula 1]

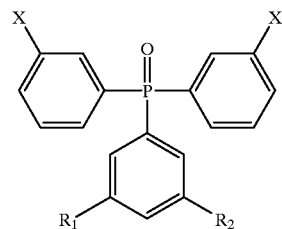

wherein $R_1$ and $R_2$ are independently a fluorine-substituted alkyl group; and X is hydrogen, a nitro group, or an amine group.

6 Claims, 7 Drawing Sheets

TRIARYLPHOSPHINE OXIDE DERIVATIVES CONTAINING FLUORINE SUBSTITUENTS

BACKGROUND OF THE INVENTION

1. Field of the Invention

The present invention relates to triarylphosphine oxide derivatives and, more particularly, to triarylphosphine oxide derivatives containing fluorine substituents that are useful as a monomer in preparation of polymers with improved properties such as chemical resistance, electrical insulating and adhesive properties, and flame retardancy.

2. Description of the Related Art

There are known methods of using bis(3-aminophenyl) phenyl phosphine oxide (DAPPO) or diaminodiphenylsulfone (DDS) as a monomer in preparation of a polymer exhibiting excellent adhesive property and flame retardancy, such as polyimide resin (See. M. F. Martinez-Nuez et al., Polymer Prepint, 35, p. 709 (1994)). However, using DDS which contains no phosphine oxide produces a polymer having a low adhesive strength and high dielectric constant and birefringence, while using DAPPO provides a polymer excellent in adhesiveness but still high in dielectric constant and birefringence.

Since fluorine (F) has very high electronegativity, small Van der Walls' radius comparable to that of hydrogen and a high bonding energy with other elements, the compound containing fluorine substituents provides low intermolecular force and thus low surface energy and low friction. Moreover, fluorine-containing compounds have excellent chemical resistance, flame resistance, heat resistance, electrical insulating property and weather resistance. Therefore, these are utilized in nuclear power plants, solar batteries, optical communications and semiconductor devices. However, the major obstacle of the fluorine-containing compounds is their poor adhesive property due to the poor sticking nature of fluorine.

Accordingly, the invention aims to provide novel triarylphosphine oxide derivatives containing fluorine substituents with improved properties by introducing fluoine substituents to phosphine oxides that are known to have high adhesive strength and flame retardancy.

SUMMARY OF THE INVENTION

It is, therefore, an object of the present invention to provide novel triarylphosphine oxide derivatives containing both fluorine and phosphor substituents that are useful in preparation of polymers with improved properties such as adhesiveness and flame retardancy as well as chemical resistance and electrical insulating property.

To achieve the above object of the invention, there is provided triarylphosphine oxide derivatives containing fluorine substituents as represented by the chemical formula 1:

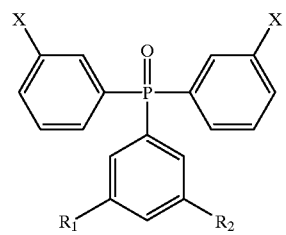

[Chemical Formula 1]

wherein $R_1$ and $R_2$ are independently a fluorine-substituted alkyl group; and X is hydrogen, a nitro group or an amine group.

There is further provided a method for preparing the triarylphosphine oxide derivatives containing fluorine substituents and a method for preparing polyimides from the derivatives.

DETAILED DESCRIPTION OF THE PREFERRED EMBODIMENT

Figure 1:
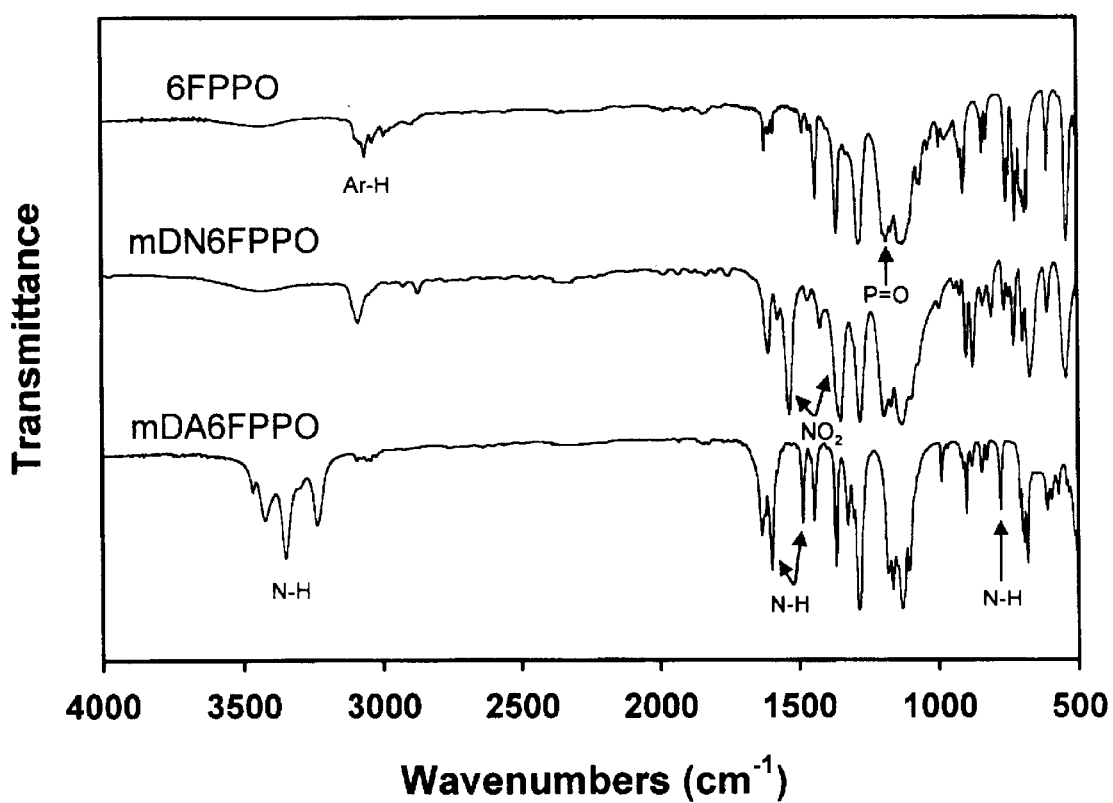
FIGS. 1 to 4 are FT-IR, $^1$H-NMR, $^{31}$P-NMR and $^{19}$F-NMR spectra of compounds synthesized in Examples 1 to 3, respectively.

Hereinafter, a detailed description will be given as to the present invention.

The present invention compound can be prepared, for example, according to the reaction formula 1:

[Reaction Formula 1]

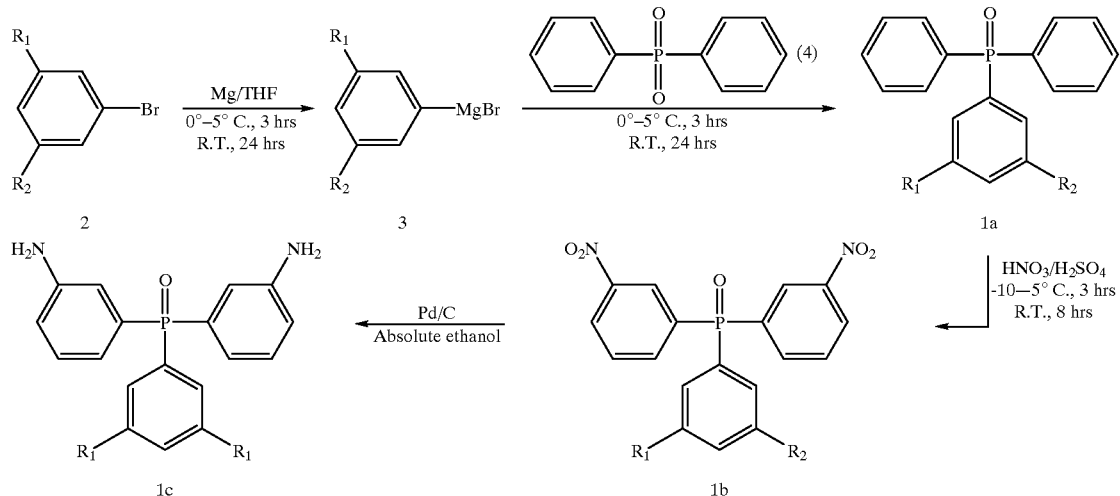

wherein $R_1$ and $R_2$ are as defined above.

More specifically, a bromobenzene containing two fluoroalkyl substituents as represented by chemical formula 2 is reacted in the presence of magnesium in an organic solvent such as tetrahydrofuran to obtain the compound of chemical formula 3, which is then reacted with diphenylphosphinic chloride represented by chemical formula 4 to produce the present invention compound of chemical formula 1a (wherein X is H) by the Grignard reaction. Here, the molar ratio of the reactants is in the range of 1:1 to 1:1.2, and the reaction is carried out at a temperature of 0 to 5° C. for 3 hours and at the room temperature for more about 24 hours.

Subsequently, the compound of chemical formula 1a is subjected to nitration of the benzene rings in the presence of a salt such as sodium chloride to produce the present invention compound represented by chemical formula 1b (wherein X is $NO_2$). here, the reaction may be carried out at a temperature of –10 to –5° C. for about 3 hours and at the room temperature for more 8 hours. the compound of chemical formula 1b is then hydrogenate3d in the presence of a palladium catalyst in an organic solvent such as alcohol to yield the present invention compound represented by chemical formula 1c (wherein X is $NH_2$).

The present invention compound of chemical formula 1 is subjected to condensation polymerization with a dianhydride compound by a known method to produce a polyamic acid, which is then solution-imidated to yield a polyimide polymer excellent in adhesiveness, chemical resistance and electrical insulating property.

Examples of the dianhydride compound used in preparation of the polyimide may include pyromellitic anhydride (PMDA), 3,4,3', 4'-benzophenone tetracarboxylic dianhydride (BTDA), 4,4'(hexafluoropropylidene) diphthalic anhydride (6FDA), 4,4'-oxydiphthalic dianhydride (ODPA) and other known compounds. The condensation polymerization of the compound of chemical formula 1 with the dianhydride compound may be performed in an organic solvent such as N-methylpyrrolidone (NMP), N,N-dimethylacetamide (DMAc) or the like. Here, a mono-functional compound such as phthalic acid can be added to the reaction mixture in order to regulate the molecular weight of the product.

Examples of the solvent as used herein for solution imidation of the polyamic acid prepared by the condensation polymerization may include NMP, o-dichlorobenzene (DCB), toluene and a mixture thereof, and preferably a mixture of NMP and DCB.

The polymers obtained from the triarylphosphine oxide derivatives of chemical formula 1 include the polyimide, polyamide, and copolymers thereof and can be prepared by a known method.

Now, the present invention will be described in further detail by way of examples, which are not to be considered as limiting the scope of the invention.

EXAMPLE 1

Preparation of {3',5'-bis(trifluoromethyl) phenyl}diphenylphosphine oxide (6FPPO) of Chemical Formula 1a 4.5 g of magnesium turnings (supplied from Aldrich Co.) and 100 ml of refluxed tetrahydrofuran (supplied from Fisher Co.) were added to a 250 ml three-necked round bottom flask equipped with a magnet stirrer, a funnel, a condenser and a nitrogen inlet tube. To the reaction mixture cooled to below 5° C. in ice water was added 23.5 ml of 3,5-bis(trifluoromethyl)bromobenzene (supplied from Aldrich Co.) through the funnel for 3 hours, the solution was slowly warmed to the ambient temperature and reacted for more 16 hours to obtain 3,5-bis(trifluoromethyl)phenyl magnesium bromide as a thick brownish liquid.

To the product cooled to below 5° C. in ice water was added diphenylphosphinic chloride (supplied from Aldrich Co.) through the funnel for 3 hours. The reaction mixture was stood until the room temperature and reacted for further 24 hours to produce a blackish brown solution.

After adding 10 ml of a 10% aqueous sulfuric acid solution, the reaction mixture was washed with 1 L of water, neutralized with sodium acid carbonate ($NaHCO_3$) and extracted with chloroform and water. The extraction liquid was distilled under vacuum to obtain a solid residue, which was then dissolved in 1 L of boiling hexane and recrystallized to obtain 45 g of the title compound (90% yield).

Figure 2:
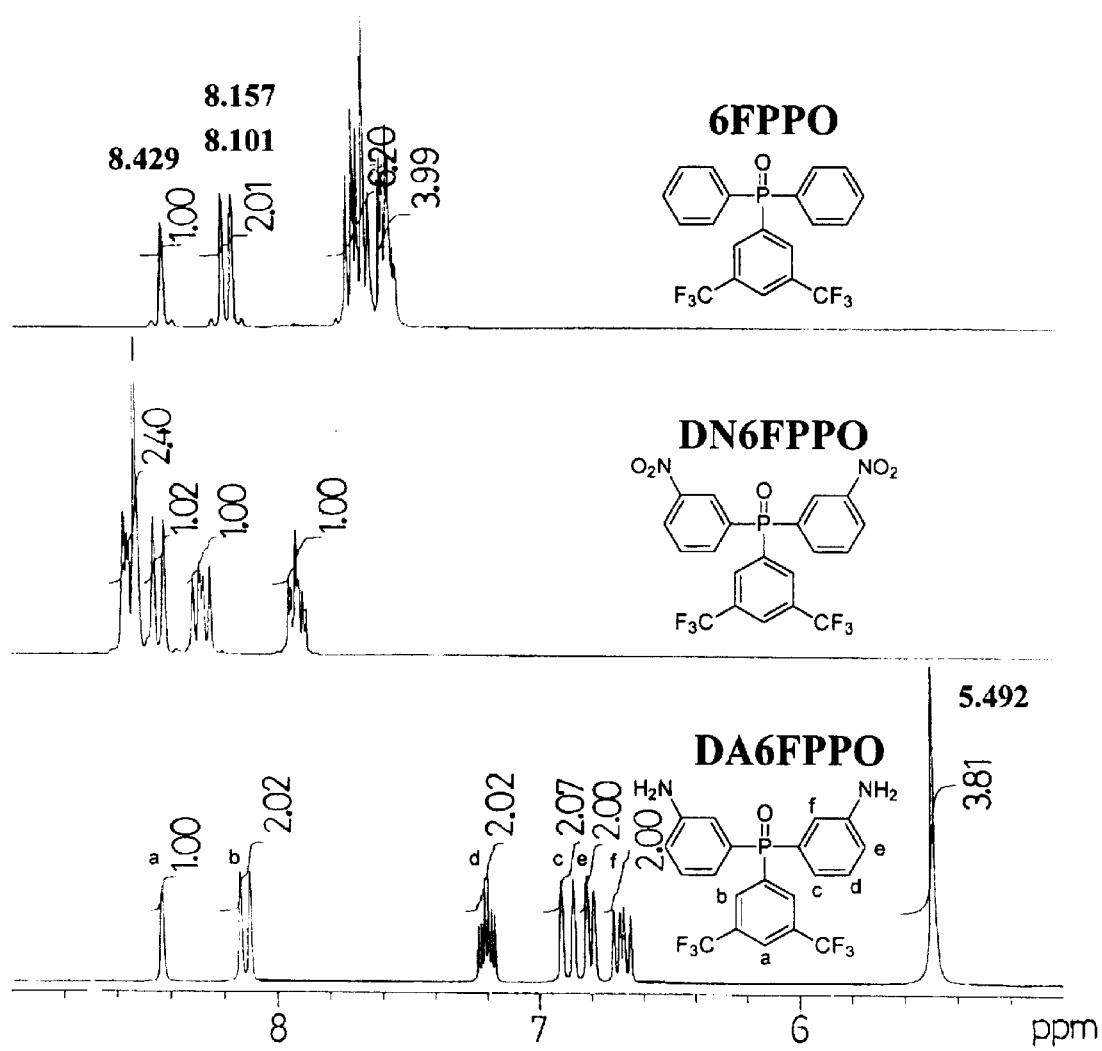
Figure 3:
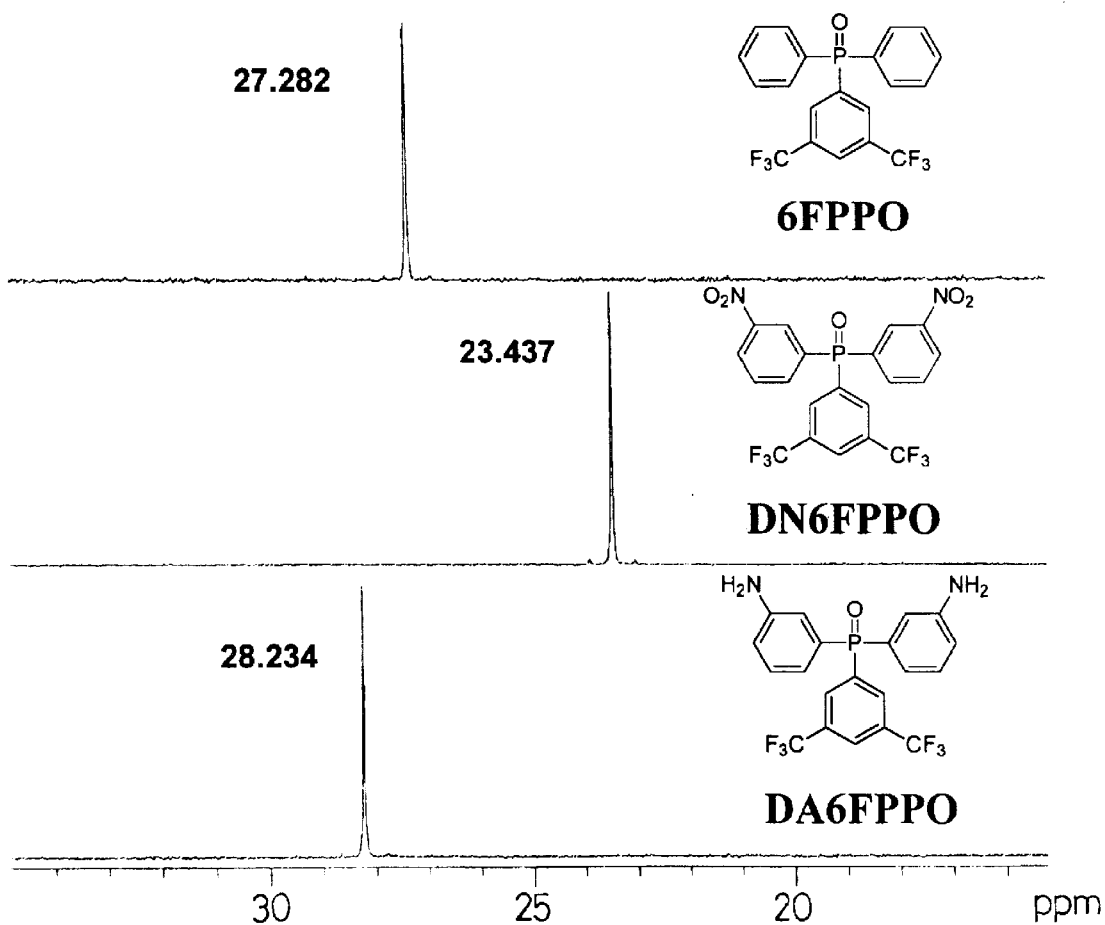
Figure 4:
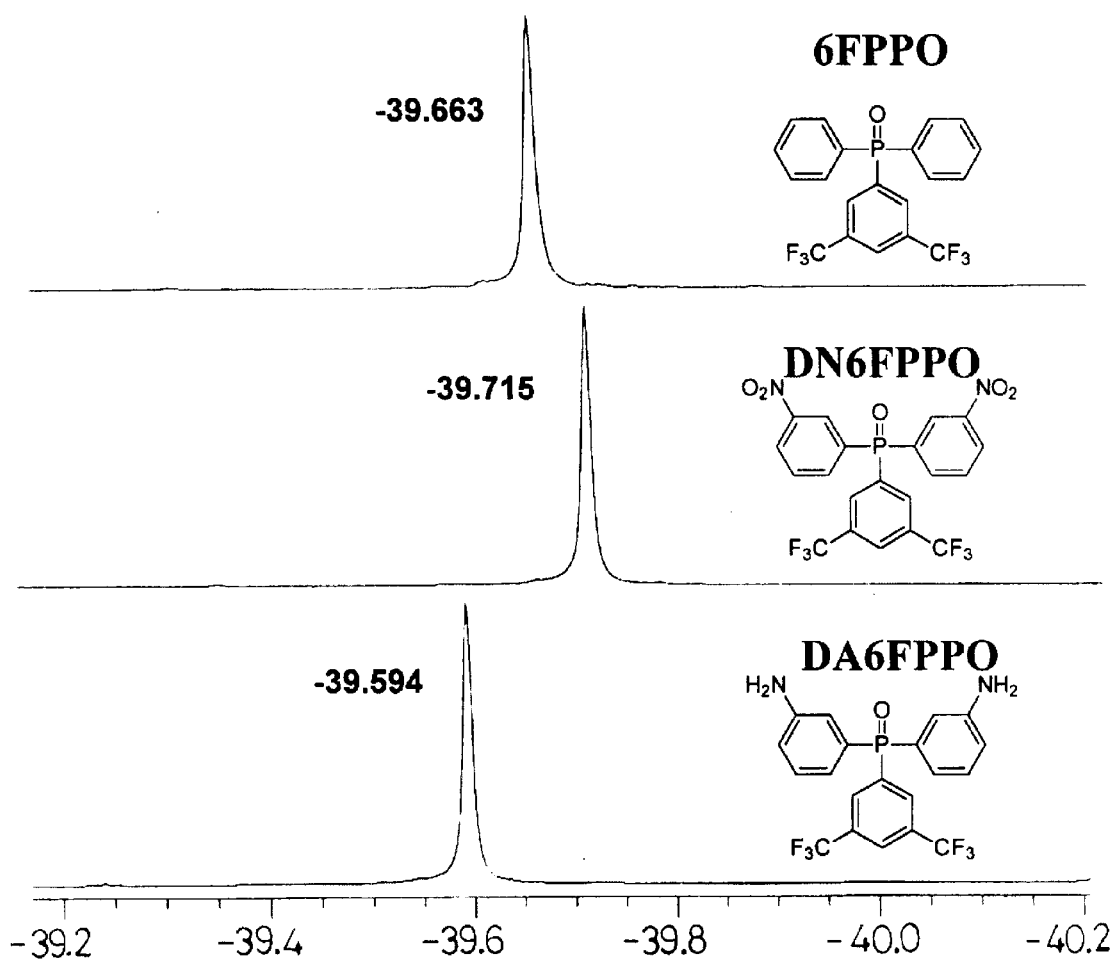

The compound obtained was dried at 60° C. in a vacuum oven for 6 hours and analyzed for melting point and FT-IR, $^1$H-NMR, $^{31}$P-NMR and $^{19}$F-NMR spectra. The melting point was determined in the range of 94.2 to 95.1° C. According to the FT-IR spectrum as shown in FIG. 1, a C-F vibration peak was observed at 1363–1500 cm$^{-1}$ and a P=O stretching peak at 1186 cm$^{-1}$. The $^1$H-NMR spectrum (solvent: DMSO-d$_6$) as shown in FIG. 2 had peaks at 8.46 ppm, 8.23 ppm and 8.20 ppm and a $^1$H peak of diphenyl at 7.55–7.77 ppm. These data identified the product as the title compound. According to the $^{31}$P-NMR and $^{19}$F-NMR spectra (solvent: CDCl$_3$) as shown in FIGS. 3 and 4, a single peak appeared at 27.282 ppm and −39.663 ppm, which also demonstrated that the product was the title compound.

EXAMPLE 2

Preparation of bis(3-nitrophenyl)-3',5'-bis (trifluoromethyl)phenyl phosphine oxide (DN6FPPO) of Chemical Formula 1b 6FPPO prepared in Example 1 was subjected to nitration of the benzene rings with nitric acid and sulfuric acid to yield the target compound. More specifically, 50 g of 6FPPO and 500 ml of sulfuric acid were added to a 1 L three-necked round bottom flask with a magnet stirrer, a funnel and a nitrogen inlet opening, and dissolved at the ambient temperature. To the reaction mixture cooled to a temperature of −10 to −5° C. with NaCl and ice was added a mixed solution of nitric acid (25 ml) and sulfuric acid (75 ml) through the funnel for 3 hours. The solution was remained at the ambient temperature and reacted for more 8 hours. After the completion of the reaction, the product is mixed with ice (1 kg) and the resulting mixture was extracted with chloroform and water at the ambient temperature.

The extract was dissolved in 1 L of boiling ethanol and recrystallized to obtain 55 g of the target compound (92% yield).

The compound thus obtained was dried at 100° C. in a vacuum oven for 6 hours and analyzed for melting point and FT-IR, $^1$H-NMR, $^{31}$P-NMR and $^{19}$F-NMR spectra. The melting point was determined in the range of 174.5 to 175.0° C. According to the FT-IR spectrum as shown in FIG. 1, there were observed an asymmetric stretching peak (at 1534 cm$^{-1}$) and a symmetric stretching peak (at 1350 cm$^{-1}$), which peaks are peculiar to aromatic nitro-compounds and not observed in 6FPPO prepared in Example 1. The $^1$H-NMR spectrum (solvent: DMSO-d$_6$) as shown in FIG. 2 had four group peaks at 7.89–8.57 ppm, demonstrating production of NO$_2$. The $^{31}$P-NMR spectrum (solvent: CDCl$_3$) as shown in FIG. 3 showed that a single peak indicating high purity of the compound shifted from 27.282 ppm to 23.432 ppm due to production of NO$_2$. also, the $^{19}$F-NMR spectrum (solvent: CDCl$_3$) as shown in FIG. 4 had a single peak at −39.715 ppm almost like that of 6FPPO because the fluorine peak was not affected by the nitration.

EXAMPLE 3

Preparation of di(3-aminophenyl) {3',5'-bis (trifluoromethyl)penyl}phosphine oxide (DA6FPPO) of Chemical Formula 1b DN6FPPO prepared in Example 2 was hydrogenated in the presence of a palladium catalyst on active carbon to obtain the target compound. More particularlly, 5 g of DN6FPPO, 250 ml of anhydrous ethanol and 2 spoons (10–15 mg) of 10 wt.% Pd/C were added to a high-pressure reactor and reacted for 24 hours under the conditions of 230 rpm, 1000 psi hydrogen pressure and 50° C. The reaction mixture was filtered with cellite to remove the active carbon and the solvent was removed by vaporization. The residual mixture was dissolved in ethyl acetate and purified on a silica-filled column, after which the solvent was removed by vaporization to obtain 4.5 g of the white target compound (90% yield).

The compound thus obtained was purified by the sublimation process and analyzed for melting point and FT-IR, $^1$H-NMR, $^{31}$P-NMR and $^{19}$F-NMR spectra. The melting point was determined in the range of 225.5 to 226.5° C. According to the FT-IR spectrum as shown in FIG. 1, there were observed stretching peaks of the primary amine at 3421 cm$^{-1}$ and 3349 cm$^{-1}$ and wide bending peaks of the primary amine at 1640–1560 cm$^{-1}$. The $^1$H-NMR spectrum (solvent: DMSO-d$_6$) as shown in FIG. 2 had peaks at 8.44 ppm, 8.14 ppm and 8.10 ppm and four group peaks at 6.60–6.74 ppm, with a single peak of the amine proton at 5.50 ppm.

According to the $^{31}$P-NMR spectrum (solvent: CDCl$_3$) as shown in FIG. 3, a single peak of P was shifted from 23.432 ppm to 28.23 ppm due to production of amine. The $^{19}$F-NMR spectrum (solvent: CDCl$_3$) as shown in FIG. 4 had a single peak of F at −39.594 ppm almost like that of 6FPPO or DN6FPPO which was slightly affected by the production of amine.

While on the other, an elementary analysis showed that the theoretical values of the individual elements were almost the same as the measured values, which demonstrated that the product was DA6FPPO. Theoretical values: C=54.06, N=6.30 and H=3.40; and measured values: C=54.02, N=6.30 and H=3.38.

EXAMPLE 4

Preparation of Polyimide.

A polyimide was prepared from the DA6FPPO as obtained in Example 3 in the following procedures.

First, 5 g of DA6FPPO and 0.008 g of phthalic acid were dried with P$_2$O$_5$ in a three-necked round bottom flask equipped with a reverse Dean-Stark trap, a drying tube, a nitrogen inlet tube and a thermometer while nitrogen is injected into the flask, in which case the flask was heated with flame prior to the reaction in order to remove moisture completely. To the reaction mixture dissolved in distilled anhydrous N-methylpyrrolidone (NP) was slowly added a dianhydride compound in an amount of 2.4153 g (for pyromellitic anhydride (PMDA)), 3.5743 g (for 3,4,3',4'-benzophenone tetracarboxylic dianhydride (BTDA)), 4.9 g (for 4,4'-(hexafluoropropylidene) diphthalic anhydride (6FDA)) or 3.4593 g (for 4,4'-oxydiphthahic dianhydride (ODPA)). Finally, NMP was added to the reaction mixture to provide a 15 w %/v solution, which was then reacted at the ambient temperature for 24 hours to obtain polyamic acid.

Subsequently, 7.5 g of the polyamic acid was subjected to solution imidation at 180–190° C. for 24 hours under the nitrogen atmosphere in a mixture of NMP and o-dichlorobenzene (DCB) at a volume ratio of 8:2. The reaction mixture was warmed to the ambient temperature and precipitated with methanol to obtain a powdery polyimide (number average molecular weight: about 20,000).

For the purpose of comparison, the polyimide was synthesized in the same manner as described above from the conventional di(3-aminophenyl)phenyl phosphine oxide (DAPPO) prepared in the procedures as stated by M. F. Martinez-Nuez et al., *Polymer Prepint*, 35, p. 709 (1994), instead of the DA6FPPO prepared in Example 3, with the diaminophenylsulfone(DDS) commercially available from Aldrich Co.

EXAMPLE 5

Measurement of Properties of Polyimide

The polyimide resins prepared in Example 4 were dried in a vacuum oven at the ambient temperature for 5 hours, at 100° C. for 5 hours, at 150° C. for 5 hours and at 200° C. for 12 hours, and analyzed for the chemical, thermal and optical properties as follows.

(1) FT-IR Analysis

Figure 5:
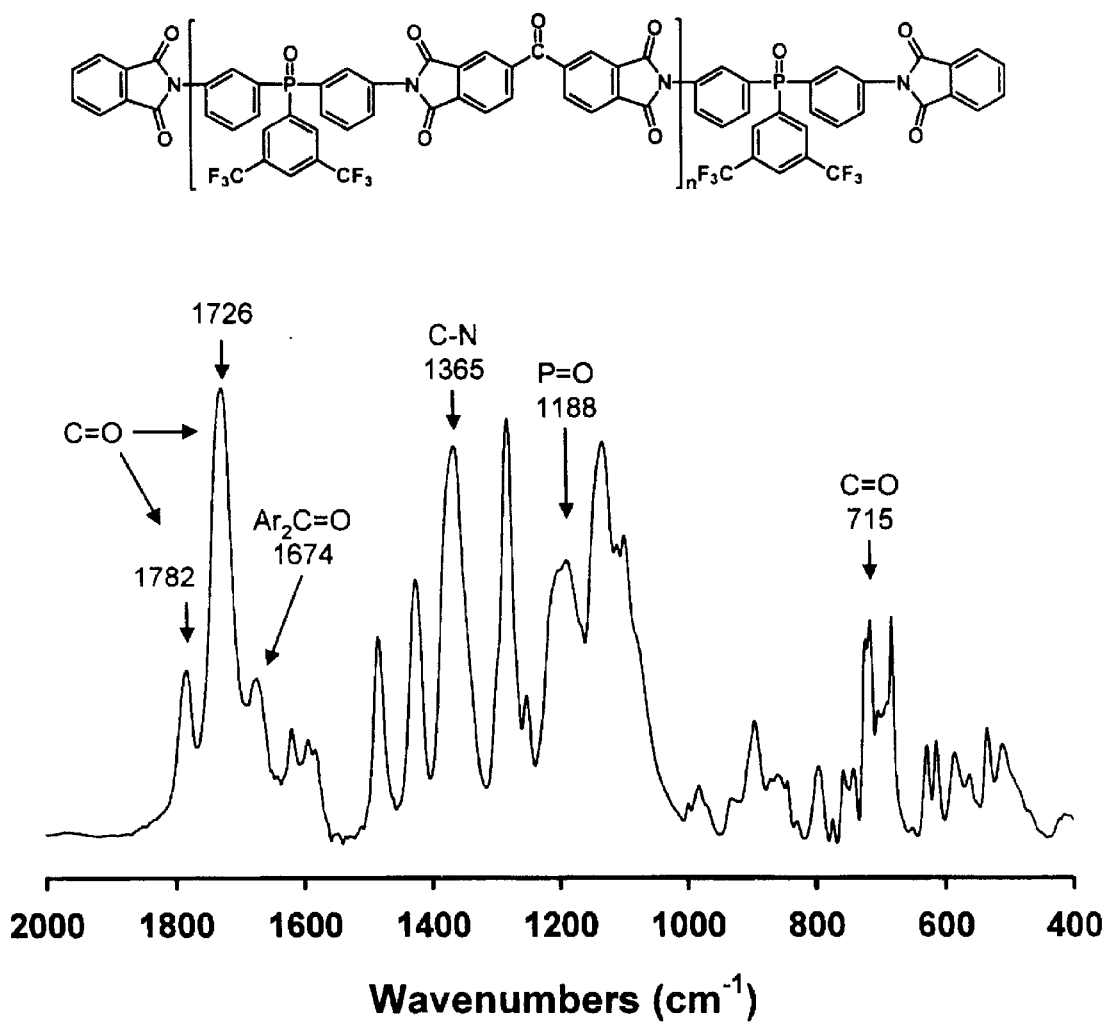
FIG. 5 is an FT-IR spectrum of polyimides prepared from the compounds of the present invention.

An FT-IR spectrometer (IR-2000, Perkin-Elmer) was used to obtain an FT-IR spectrum as shown in FIG. 5.

It can be seed from FIG. 5 that the DA6FPPO-based polyimide synthesized according to the present invention has absorption peaks peculiar to amides at 1782 cm$^{-1}$, 1726 cm$^{-1}$ and 715 cm$^{-1}$ for C=O, at 1365 cm$^{-1}$ for C—N and at 1188 cm$^{-1}$ for P=O and that 100% imidation has been achieved.

(2) Intrinsic Viscosity

This property was determined with a Canon Ubbelohde viscometer using NMP as a solvent at 25° C. The results are presented in Table 1. It can be seen from Table 1 that the present invention polyimide has the almost same molecular weight as the comparative polyimides.

(3) Differential Scanning Calorimetry (DSC)

The glass transition temperature Tg was determined with a differential scanning calorimeter (TA-2910) at 10° C./min under the nitrogen atmosphere. The results are presented in Table 1.

It can be seen from Table 1 that the DA6FPPO-based polyimide prepared according to the present invention has a glass transition temperature Tg in the range of 228 to 281° C. and that the glass transition temperature Tg of the polymer increases with an increase in the chain rigidity in the increasing order of ODPA, BTDA, 6FDA and PMDA. As for the comparative polyimides, the glass transition temperature was 266° C. for BTDA-DDS and 273° C. for BTDA-DAPPO. It is considered that the BTDA-DA6FPPO of the present invention has a lower glass transition temperature than those of the conventional polyimides, BTDA-DAPPO and BTDA-DDS because the fluorine substituents of the DA6FPPO increase the free volume of the polyimide.

(4) Thermogravimetric Analysis (TGA)

The polyimide dried at a temperature of Tg plus 50° C. was adhered on a hot press for 5 minutes and pressed under 300 psi for 10 minutes to obtain a 0.1 mm thick flexible polyimide film. The film was light brown-colored and gets more transparent with an increase in the fluorine content. The results of the thermogravimetric analysis are presented in FIGS. 6 and 7 and Table 1 (in terms of temperature Td at a loss of 5 wt. %).

Figure 6:
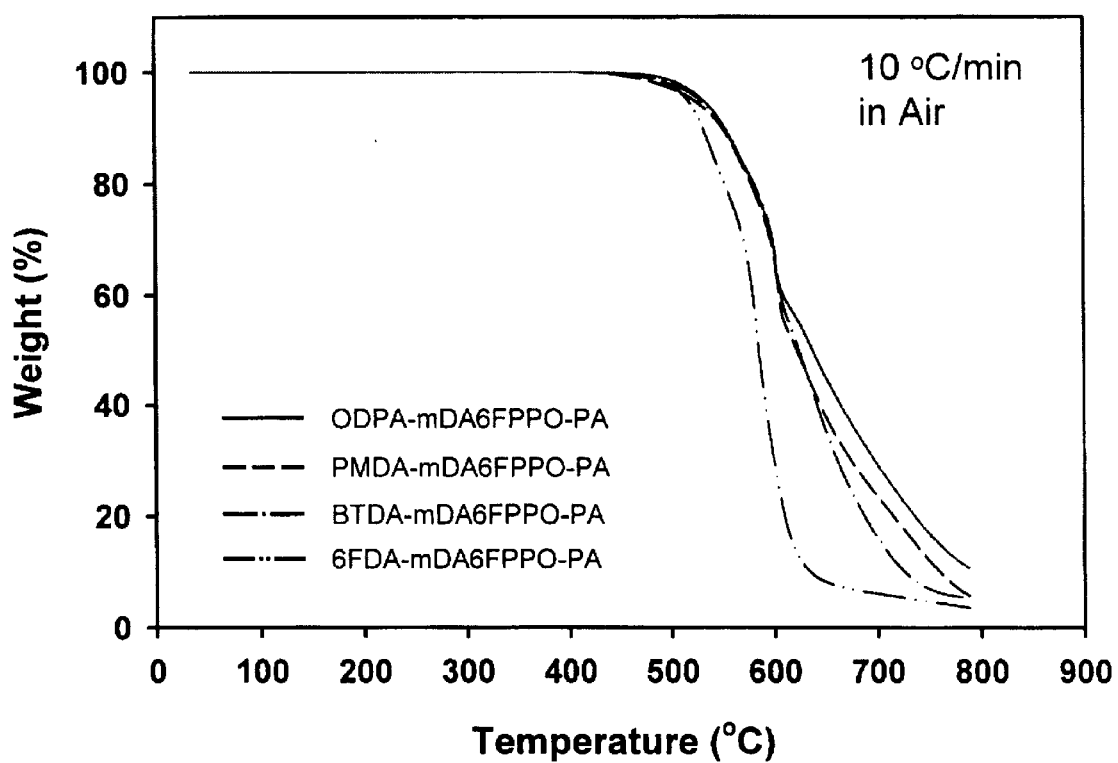
FIG. 6 is a graph obtained from a Thermo Gravimetric analysis of the polyimides prepared from the compounds of the present invention.
Figure 7:
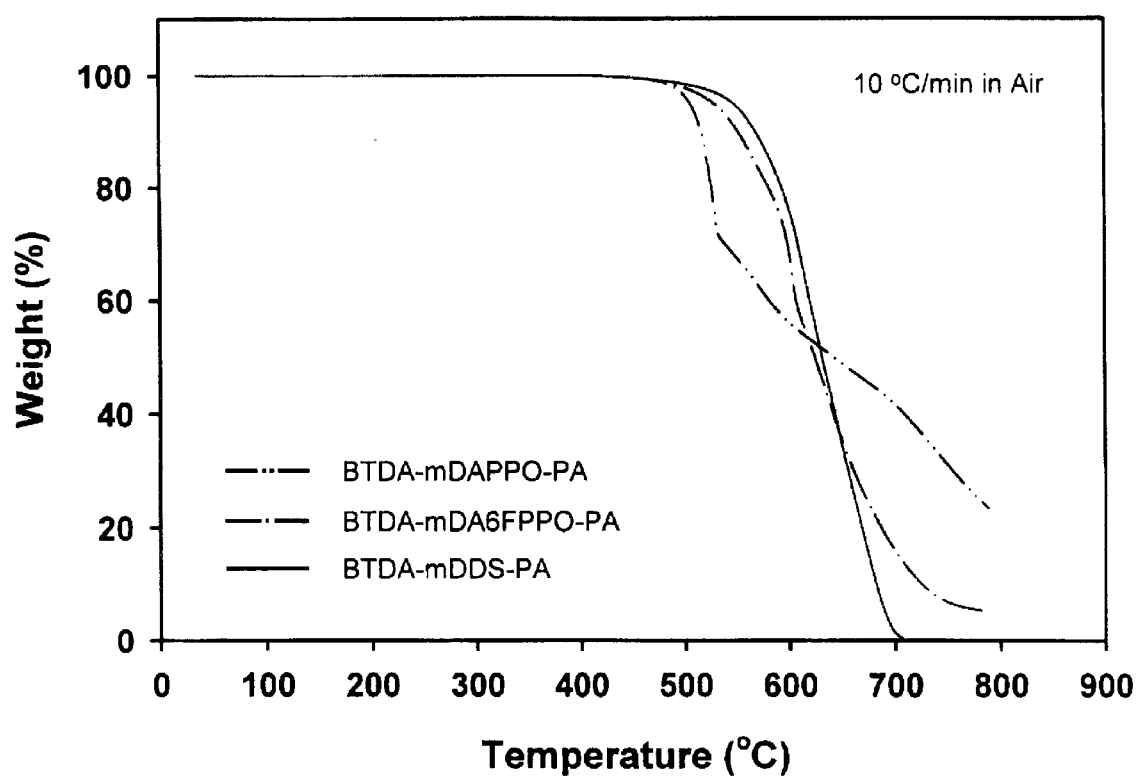
FIG. 7 is a comparative graph obtained from a Thermo Gravimetric analysis of polyimides prepared from the present invention compounds in comparison with polyimides prepared from the conventional compounds.

As seen from the data of FIGS. 6 and 7 and Table 1, the DA6FPPO-based polyimide of the present invention had no weight loss until 400° C. and the thermal stability was increased depending on the type of the dianhydride compound in the order of 6FDA, BTDA, PMDA and ODPA. Especially, the 6FDA-DA6FPPO has a low thermal stability in relation to the other DA6FPPO-based polyimides because it has a relatively low content of phosphine oxide, which is known to be thermally stable due to a high molecular weight of 6FDA compared to the other dianhydrides. It can be seen that about 5 to 15 wt.% of the DA6FPPO-based polyimide remained even at 800° C. and that the DA6FPPO-based polyimide of the present invention was superior in thermal stability to the comparative polyimides,

TABLE 1

| Monomers used for Polyimides | | Tg (° C.) | Td (° C.) | Intrinsic Viscosity (dl/g) |
|---|---|---|---|---|
| DA6FPPO | 6FDA | 247 | 517 | 0.24 |
|  | BTDA | 243 | 530 | 0.28 |
|  | ODPA | 228 | 533 | 0.22 |
|  | PMDA | 281 | 522 | 0.20 |
| DAPPO | 6FDA | 271 | 524 | 0.29 |
|  | BTDA | 273 | 506 | 0.30 |
|  | ODPA | 251 | 526 | 0.27 |
|  | PMDA | 331 | 479 | 0.20 |
| DDS | BTDA | 266 | 548 | 0.26 |

(5) Solubility in Different Solvents

To measure the solubility in different solvents, 0.2 g of the polyimide film prepared as in the thermogravimetric analysis was immersed in 10 ml of an organic solvent and observed at the room temperature for 24 hours. The test results depending on type of the organic solvent are presented in Table 2.

TABLE 2

| Monomers used for Polyimides | | Organic Solvents | | | | | | |
|---|---|---|---|---|---|---|---|---|
|  |  | MMP | DMAc | TCE | CHCl$^3$ | THF | Toluene | Acetone |
| DA6FPPO | 6FDA | S | S | S | S | S | I | S |
|  | BTDA | S | S | S | S | P | S | I |
|  | ODPA | S | S | S | S | S | P | I |
|  | PMDA | S | S | S | S | P | I | I |
| DAPPO | 6FDA | S | S | S | S | S | I | P |
|  | BTDA | S | S | S | S | I | S | I |
|  | ODPA | S | S | P | S | P | I | I |
|  | PMDA | S | S | S | P | I | I | I |
| DDS | 6FDA | S | S | P | P | I | I | I |
|  | BTDA | S | S | I | I | I | I | I |
|  | ODPA | S | S | I | I | I | I | I |
|  | PMDA | I | I | I | I | I | I | I |

Note)
S: Soluble;
P: Partially Soluble; and
I: Insoluble.

As seen from Table 2, the DA6FPPO-based polyimide of the present invention was soluble in NMP, DMAc (dimethylacetamide), TCE (trichloroethane) and chloroform (CHCl$_3$) and entirely or partially soluble in THF (tetrahydrofuran) and toluene. Especially, 6FDA-DA6FPPO was dissolved in acetone. Contrarily, as for the comparative polyimides, the DAPPO-based polyimide was soluble in NMP and DMAc and entirely or partially soluble in TCe and chloroform, and the DDS-based polyimide was soluble only in NMP and DMAc and insoluble in the other solvent.

Such a high solubility of the present invention polyimide is considered advantageous in that the typical polyimide, i.e., Kapton $^R$(PMDA-ODA) (oxydianiline)-based polyimide) is insoluble in many organic solvents and inferior in workability.

(6) Optical Properties

A thin film prepared by spin-coating the polyimide solution (14 wt. % in TCE) on an Si wafer was measured for refractive index with a Metricon Model 2010 Prism Coupler. The results are presented in Table 3.

TABLE 3

| Monomers used for Polyimides | | Dielectric constant ($\epsilon$) | Refractive Index | | Birefringence ($n_1-n_2$) |
|---|---|---|---|---|---|
| | | | In Plane | Out of Plane | |
| A6FPPO | FDA | 2.355 | 1.5351 | 1.5340 | 0.0011 |
| | TDA | 2.502 | 1.5836 | 1.5803 | 0.0033 |
| | DPA | 2.505 | 1.5835 | 1.5818 | 0.0017 |
| APPO | FDA | 2.495 | 1.5804 | 1.5787 | 0.0017 |
| | TDA | 2.698 | 1.6432 | 1.6418 | 0.0014 |
| | DPA | 2.696 | 1.6832 | 1.6408 | 0.0024 |
| | MDA | 2.827 | 1.6827 | 1.6800 | 0.0027 |
| Kapton ODA + PMD | | 2.756 | 1.72 | 1.60 | 0.12 |

Note) See. T. P. Russel et al., J. Polm. Sci., *Polym. Phys.*, 21, 1745 (1983).

It is considered from Table 3 that the 6FDA-DA6FPPO having a high fluorine content according to the present invention has a low dielectric constant ($\epsilon$) of 2.355 relative to the PMDA-ODA whose dielectric constant is 2.756, and that the dielectric constant is not significantly affected by phosphine oxide.

As also seen from Table 3, in regard to the birefringence which is the one of the most important properties in using the polyimide as a material for optical devices, the 6FDA-DA6FPPO containing both fluorine and phosphine oxide according to the present invention has a birefringence of 0.0011 about 100 times as low as that of the PMDA-ODA (0.12). It can be seen that the birefringence is decreased with the higher content of fluorine or phosphine oxide, more potently with an increase in the phosphine oxide content, since the triphenylphosphine oxide is not present in the same plane.

Due to low dielectric constant and high birefringence, the DA6FPPO-based polyimide containing both fluorine and phosphine oxide according to the present invention is considered useful for semiconductor packaging or optical devices.

(7) Adhesiveness

A Cu foil and a Cr/silane-coated Cu foil (UCF ICF-STD. IY) being 0.035 mm in thickness and supplied form Iljin Copper oil Co. were used to perform a T-peel test according to ASTM D1876. The results are presented in Table 4. The T-peel test was carried out under the following adhesive conditions: adhesion temperature being the polyimide's glass transition temperature Tg plus 50° C., pressure of 1000 psi, time period of 30 minutes and adhesive coating thickness of 0.02±0.002 mm.

TABLE 4

| | Adhesive Strength (g/mm) | |
|---|---|---|
| | Cr-Silane-coated Cu Foil | Uncoated Cu Foil* |
| BTDA-DA6FPPO | 93.31 ± 2.49 | 50.96 ± 1.30 |
| BTDA-DAPPO | 108.45 ± 1.92 | 51.30 ± 3.78 |
| BTDA-DDS | 73.08 ± 6.87 | 34.56 ± 0.68 |

*Tested after Etching with Strong Acid.

As seen from Table 4, for the Cr/silane-coated Cu foil, the BTDA-DAPPO of the highest phosphine oxide content had an adhesive strength of 108.45 g/mm higher than that of the BTDA-DDS containing no phosphine oxide (73 g/mm) by about 35 g/mm. Although fluorine-containing polymers are known to be poor in adhesiveness due to fluorine substituents, the BTDA-DA6FPPO containing boh fluorine and phosphine oxide according to the present invention had a high adhesive strength of 93.31/mm than that of the BTDA-DDS by 20 g/mm. strength of 93.31/mm than that of the TDA-DDS by 20 g/mm.

For the uncoated Cu foil, the BTDA-DAPPO containing phosphine oxide also had a high adhesive strength of 51.3 g/mm than that of the BTDA-DDS (34.56 g/mm), which demonstrated that the polyimide containing phosphine oxide had a high adhesive strength. It is therefore considered that adding phosphine oxide may allow the polyimide containing fluorine to have a high adhesive strength.

As described above, the triarylphosphine oxide derivatives containing fluorine substituents according to the present invention can be used for preparation of a polymer excellent in chemical resistance and electrical insulating property as well as adhesiveness and flame retardancy. The resulting polymer is also useful as a semiconductor packaging material, a refractory material, and an intermediate material for optical fiber and devices, and an adhesive for metals.

What is claimed is:

1. A compound of chemical formula 1;

[Chemical Formula 1]

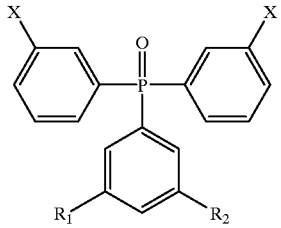

wherein $R_1$ and $R_2$ are independently a fluorine substituted alkyl group; and X is hydrogen, a nitro group, or an amine group.

2. A method for preparing a compound represented by the chemical formula 1a comprising the step of reacting 3,5-di (fluoroalkyl)bromobenzene with diphenylphosphinic chloride at a molar ratio of 1:1 to 1:1.2 in an organic solvent and magnesium;

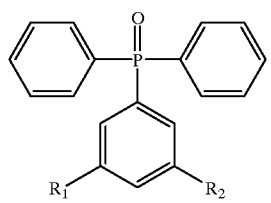

wherein R₁ and R₂ are independently a fluorine substituted alkyl group.

3. A method for preparing a compound represented by the chemical formula 1b comprising the steps of:
reacting 3,5-di(fluoroalkyl)bromobenzene with diphenylphosphinic chloride at a molar ratio of 1:1 to 1:1.2 in an organic solvent and magnesium to obtain a compound represented by the chemical formula 1a;
nitrating the benzene rings of the compound of the chemical formula 1a in the presence of a salt to obtain a compound represented by the chemical formula 1b;

[Chemical Formula 1a]

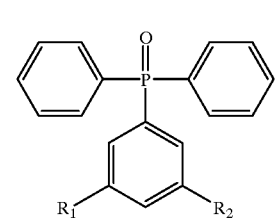

[Chemical Formula 1b]

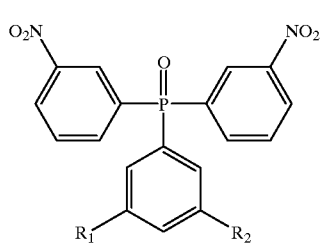

wherein R₁ and R₂ are independently a fluroine substutited alkyl group.

4. A method for preparing a compound represented by the chemical formula 1c comprising the steps of:
reacting 3,5-di-(fluoroalkyl)bromobenzene with diphenylphosphinic chloride at a molar ratio of 1:1 to 1:1.2 in an organic solvent and magnesium to obtain a compound represented by the chemical formula 1a;
nitrating the benzene rings of the compound of the chemical formula 1a in the presence of a salt to obtain a compound represented by the chemical formula 1b; and
hydrogenating the compound of the chemical formula 1b in the presence of a palladium catalyst in an organic solvent;

[Chemical Formula 1a]

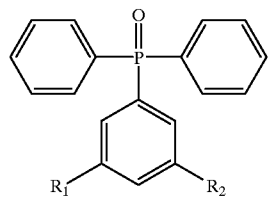

[Chemical Formula 1b]

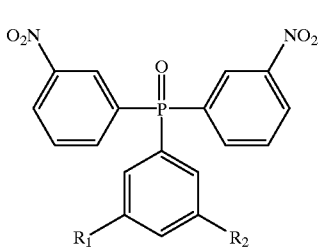

[Chemical Formula 1c]

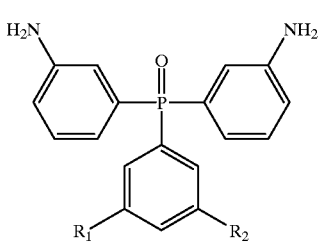

wherein R₁ and R₂ are independently a fluorine substitued alkyl group.

5. A method for preparing a polyimide polymer comprising the steps of reacting a compound of chemical formula 1 according to claim 1 with a dianhydride compound, and performing a solution imidation on results of said reaction.

6. The method as claimed in claim 5, wherein the dianhyride compound is selected from the group consisting of pyromellitic anhydride(PMDA),3,4,3',4'-benzophenone tetracarboxylic dianhydride (BTDA), 4,4'-(hexafluoropropylidene)diphthalic anhydride (6FDA),4,4'-oxydiphthalic anhydride (ODPA) and mixtures thereof.

* * * * *